(12) United States Patent
Ramsbottom et al.

(10) Patent No.: US 7,368,441 B2
(45) Date of Patent: May 6, 2008

(54) METHOD OF INCREASING INTRACELLULAR CONCENTRATIONS OF PHOSPHATE AND INCREASING THE FORCE OF MUSCULAR CONTRACTIONS

(75) Inventors: James D. Ramsbottom, Mississauga (CA); Jason R. Peters, Mississauga (CA); Shan Chaudhuri, Mississauga (CA)

(73) Assignee: Aplodan Formulations Ltd., Mississauga (CA)

( * ) Notice: Subject to any disclaimer, the term of this patent is extended or adjusted under 35 U.S.C. 154(b) by 0 days.

(21) Appl. No.: 11/468,605

(22) Filed: Aug. 30, 2006

(65) Prior Publication Data

US 2008/0058288 A1    Mar. 6, 2008

(51) Int. Cl.
*A61K 31/66* (2006.01)
(52) U.S. Cl. ....................................... 514/114
(58) Field of Classification Search ............... None
See application file for complete search history.

(56) References Cited

U.S. PATENT DOCUMENTS

| 4,012,467 | A | 3/1977 | Allievi |
| 4,376,117 | A | 3/1983 | Godfraind et al. |
| 6,602,512 | B1 | 8/2003 | Cavazza |
| 2005/0192183 | A1 | 9/2005 | Gastner et al. |

FOREIGN PATENT DOCUMENTS

| BE | 666891 | 3/1965 |
| IT | 1213519 | 12/1989 |

OTHER PUBLICATIONS

International Search Report, PCT/CA2006/001428, International filing date of Aug. 30, 2006, Aplodan Formulations Ltd. et al.

*Primary Examiner*—Raymond J. Henley, III
(74) *Attorney, Agent, or Firm*—Fitzpatrick, Cella, Harper & Scinto

(57) ABSTRACT

The present invention relates to a method of increasing the intracellular concentration of phosphate by employing 2-(carbamimidoyl-methyl-amino)ethoxyphosphonic acid as vehicle and method to transport Phosphate into the cell. The increase in intracellular phosphate increases the availability of Adenosine Triphosphate and phosphocreatine, thereby leading to an increase in the anaerobic energy supply resulting in longer endurance and more forceful muscular contractions.

12 Claims, No Drawings

METHOD OF INCREASING INTRACELLULAR CONCENTRATIONS OF PHOSPHATE AND INCREASING THE FORCE OF MUSCULAR CONTRACTIONS

FIELD OF THE INVENTION

The present invention relates to a method of increasing the intracellular concentration of phosphate. Moreover, the increase in intracellular phosphate increases the availability of Adenosine Triphosphate (ATP) and phosphocreatine, thereby leading to longer endurance and more forceful muscular contractions.

BACKGROUND

Phosphate, or phosphorus, is the second most abundant mineral in the body with calcium being the most abundant. As a Phosphate salt with calcium, Phosphate is involved in the formation of bone and teeth. In other salt complexes, Phosphate is involved in acid-base balance. Phosphate is also important for the structures of DNA and cell membranes however, one of the most important roles of Phosphate is energy production in muscle as ATP and Phosphocreatine. Phosphate is also part of a compound in red blood cells known as 2, 3 DPG (2,3-diphosphoglycerate), which facilitates the release of oxygen to the muscle tissues.

Supplemental Phosphate salts have been shown to increase the concentration of 2,3 DPG in red blood cells, increasing VO2 max (a measure of aerobic fitness and a reduction in the production of lactate (Cade R, et al. Med Sci Sports Exerc. (1984) June; 16(3):263-8). Moreover, Phosphate has also been shown to enhance oxygen uptake and run performance without affecting the level of 2, 3 DPG (Kreider R B, et al. Med Sci Sports Exerc. (1990) April; 22(2):250-6). The metabolic rate can also be increased by Phosphate supplementation (Nazar K, et al. J Physiol Pharmacol. (1996) June; 47(2):373-83).

It has been noted that 86% of body's supply of phosphate is stored in the bone, 14% exists in the in the somatic cells and only 0.3% existing in the extracellular space. Therefore, with such small amounts of phosphate existing in the somatic cells and extracellular space the supply of phosphate in the body can be rapidly depleted during periods of strenuous muscle contraction or muscular loads.

Natural phosphate enhancement can be achieved through diet and supplement consumption. However, because the majority of phosphate within a body is stored in the bone an increase in phosphate, which is useful for cellular energetics through diet or direct supplementation alone, provides little if any increase in available phosphate to the somatic cells and extracellular space. Without an increase of the intracellular concentration of phosphate the energy required for muscle contraction will be quickly exhausted during physical activity. The energy requirements of contracting muscles involved in high-intensity exercise may increase 100-fold relative to resting muscles, exceeding the aerobic energy production capacity of the cells (Westerblad H, et al. News Physiol Sci. (2002) February; 17:17-21). In this case anaerobic metabolism will provide additional energy. However, high-intensity exercise results in an eventual reduced capacity for muscle contractile function, or fatigue. Thus, there is seemingly a link between anaerobic metabolism and fatigue.

In a 2000 review on the role of creatine in skeletal muscle, Casey and Greenhaff provide a thorough overview of energy supply and utilization in muscle (Casey A, et al. Am J Clin Nutr. (2000) August; 72(2 Suppl):607S-17S). Adenosine Triphosphate (ATP) is the direct energy source for contracting muscle as energy for muscle contraction is released from the dephosphorylation of ATP to yield Adenosine Diphosphate (ADP) and inorganic phosphate ($HPO_4^{2-}$ or $PO_4^{3-}$ or Pi) in the following reaction:

$$ATP + H_2O \rightarrow ADP + Pi + H^+ + energy \qquad \text{(reaction 1)}$$

Therefore, the function of muscle is largely dependent on the availability of ATP. However, the concentration of ATP available in muscle at rest prior to the start of exercise is only enough to supply about 1-2 seconds of intense activity. ATP can be readily regenerated through the anaerobic dephosphorylation of available phosphocreatine. However, like ATP, the concentration of phosphocreatine in muscle is low and only enough to sustain muscle activity for about another 6 seconds. After repeated bouts of contraction, muscle phosphocreatine levels become nearly depleted (Greenhaff P L, et al. J. Physiol. (1993) January; 460:443-53). Fatigue, although likely multifaceted in terms of biochemical events, is the point at which the energy required by contracting muscle exceeds the level available either from the stored supply of ATP or the indirect synthesis of high-energy ATP through phosphocreatine dephosphorylation.

The enzyme Creatine Kinase (CK) catalyzes the following reaction to regenerate phosphocreatine:

$$ATP + creatine \leftrightarrow ADP + phosphocreatine + H^+ \qquad \text{(reaction 2)}$$

Reaction 2 is reversible depending on the energy state of the cell. In fast-twitch skeletal muscles, a large pool of phosphocreatine is available for immediate regeneration of ATP hydrolyzed during short periods of intense muscle contraction. Due to high CK activity in these muscles, the CK reaction remains in a near-equilibrium state, keeping the concentration of [ADP] and [ATP] almost constant over several seconds at the expense of phosphocreatine.

As can be noted from examination of reactions 1 and 2, a requirement of the regeneration of both ATP and phosphocreatine is a phosphate. Supplemental phosphate counters the chemically-induced reduction of ATP in rats (Rawson N E, et al. (1994) June; 266(6 Pt 2):R1792-6) and improves athletic performance in humans concomitant with increased cardiac function and aerobic capacity (Kreider R B, et al. Int J Sport Nutr. (1992) March; 2(1):20-47). Thus, ensuring adequate supply of intracellular, intercellular, extracellular and intra-tissue phosphate may decrease the reliance on anaerobic metabolism to regenerate ATP, thereby allowing ample regeneration of phosphocreatine stores, even during times of strenuous physical activity.

Therefore there is a need to supply the body with intracellular, intercellular, extracellular and intra-tissue supplemental amounts of phosphate to increase the availability of ATP and phosphocreatine, thereby aiding in periods when strenuous muscular contractions are desired.

SUMMARY OF THE INVENTION

The foregoing needs and other needs and objectives that will become apparent for the following description are achieved in the present invention, which comprises, a method of increasing the intracellular and intra-tissue levels of phosphate in a mammal. Furthermore, the method of increasing phosphate concentrations within a given tissue, comprises the administration of 2-(carbamimidoyl-methyl-amino)ethoxyphosphonic acid, wherein said 2-(carbamimidoyl-methyl-amino)ethoxyphosphonic acid acts as a phosphate donor to increase the relative concentrations of adenosine ATP to that of ADP as well as phosphocreatine to creatine.

DETAILED DESCRIPTION OF THE INVENTION

In the following description, for the purposes of explanation, numerous specific details are set forth in order to provide a thorough understanding of the present invention. It will be apparent, however, to one skilled in the art that the present invention may be practiced without these specific details.

The present invention is directed towards a method of increasing the amount of phosphate within a cell wherein the relative concentration of ATP to ADP is increased via the administration of 2-(carbamimidoyl-methyl-amino)ethoxyphosphonic acid.

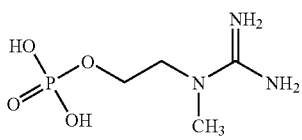

2-(carbamimidoyl-methyl-amino)ethoxyphosphonic acid 2-(carbamimidoyl-methyl-amino)ethoxyphosphonic acid is a phosphoric ester derivative of creatine. 2-(carbamimidoyl-methyl-amino)ethoxyphosphonic acid has been shown to be well tolerated and without side effects (Melloni G F, et al. Arzneimittelforschung. (1979) 29(9a):1447-9). Early studies of 2-(carbamimidoyl-methyl-amino)ethoxyphosphonic acid explored its use as a treatment for heart lesions and to restore reduced cardiac contractile function, particularly after hypoxia. (Godfraind T, et al. (1984) 34(9):968-72). 2-(carbamimidoyl-methyl-amino)ethoxyphosphonic acid has been successfully used to improve cardiac parameters in patients with inadequate coronary blood flow (Barlattani M, et al. (1979) 29(9a):1483-5).

In terms of the metabolism of 2-(carbamimidoyl-methyl-amino)ethoxyphosphonic acid, it is known that 2-(carbamimidoyl-methyl-amino)ethoxyphosphonic acid administration in humans increases urine levels of creatinine, the end metabolite and degradation product of creatine and phosphocreatine, which diffuses out of cells for excretion by the kidneys (Melloni G F, et al. Arzneimittelforschung. (1979) 29(9a): 1447-9). Creatinine is also formed by a spontaneously occurring reaction:

phosphocreatine→creatinine+$H_2O$+Pi  (reaction 3)

The detection of increased creatinine resulting from 2-(carbamimidoyl-methyl-amino)ethoxyphosphonic acid administration indicates that 2-(carbamimidoyl-methyl-amino)ethoxyphosphonic acid may serve as a source of physiological creatine, which provides well-established benefits to muscle metabolism and athletic performance mainly through the regeneration of phosphocreatine. However, 2-(carbamimidoyl-methyl-amino)ethoxyphosphonic acid as a source of creatine alone still requires a phosphate to form phosphocreatine, which in turn is the direct energy source for muscle contraction. Naturally, this phosphate would have to be drawn from a pool of available phosphate within the body, thereby reducing the availability of phosphate within the body for use in other reactions.

Advantageously, 2-(carbamimidoyl-methyl-amino)ethoxyphosphonic acid contains within it both creatine and phosphate to necessitate the regeneration of phosphocreatine. Oral administration in test animals reveals that 2-(carbamimidoyl-methyl-amino)ethoxyphosphonic acid is optimally absorbed by the intestine up to about 60% at 48 hours (Marzo A, et al. Clin Ter. (1972) Sep. 15; 62(5):419-30). 2-(carbamimidoyl-methyl-amino)ethoxyphosphonic acid was also advantageously found to be stable in both alkaline and acidic solutions, which is desirable for oral administration in animals. Moreover, via in vitro testing, it has been suggested that 2-(carbamimidoyl-methyl-amino)ethoxyphosphonic acid is dephosphorylated to creatine to some degree in the kidney, intestine and liver, and less so in the blood and muscle. Therefore, oral administration of 2-(carbamimidoyl-methyl-amino)ethoxyphosphonic acid is expected to result in fractions of both intact 2-(carbamimidoyl-methyl-amino)ethoxyphosphonic acid and dephosphorylated 2-(carbamimidoyl-methyl-amino)ethoxyphosphonic acid reaching the muscle, further signifying that intact 2-(carbamimidoyl-methyl-amino)ethoxyphosphonic acid exerts some unique beneficial effects in addition to supplying additional creatine.

Clinical trials have shown that 2-(carbamimidoyl-methyl-amino)ethoxyphosphonic acid has effects related to skeletal muscle performance similar to creatine. 2-(carbamimidoyl-methyl-amino)ethoxyphosphonic acid has been shown to improve muscle development and increase the capacity to perform physical activity. In one study, hand strength was improved by 2-(carbamimidoyl-methyl-amino)ethoxyphosphonic acid administration and while remaining unaffected in a placebo group (Nicaise J, Curr Ther Res Clin Exp. (1975) 17(6):531-4). In another study conducted in elderly subjects, it was found that 2-(carbamimidoyl-methyl-amino) ethoxyphosphonic acid improved muscular performance (Cavalieri U, et al. Clin Ther. (1974) 69: 215-223).

Thus the beneficial effects afforded by 2-(carbamimidoyl-methyl-amino)ethoxyphosphonic acid is understood to be a two-fold scheme whereby 2-(carbamimidoyl-methyl-amino) ethoxyphosphonic acid 1) serves as a source of phosphate through a dephosphorylated fraction; and 2) acts as intact molecule with unique activity compared to phosphocreatine.

The beneficial effects related to 2-(carbamimidoyl-methyl-amino)ethoxyphosphonic acid that have heretofore been undocumented in relation to creatine alone, is in part due to the unique structure and properties of 2-(carbamimidoyl-methyl-amino)ethoxyphosphonic acid i.e. the presence of the phosphate moiety and its sparring effects on depletion of the phosphate pool for energy. This may beneficially affect both resting levels of energy stores by 'priming' the muscles' energy stores prior to activity and actively contracting muscles during periods of strenuous physical activity by more efficient regeneration of energy stores.

It is herein understood that the administration of 2-(carbamimidoyl-methyl-amino)ethoxyphosphonic acid leads to an increase in the intracellular, intercellular, extracellular and intra-tissue concentration of phosphate as it has been shown to be absorbed well in the intestine following oral administration. $^{14}$C radiolabel studies of 2-(carbamimidoyl-methyl-amino)ethoxyphosphonic acid were preformed to determine the absorption and distribution of 2-(carbamimidoyl-methyl-amino)ethoxyphosphonic acid in Guinea-Pig following intravenous, intramuscular and oral administration. Significant amounts of $^{14}$C radio-labeled 2-(carbamimidoyl-methyl-amino)ethoxyphosphonic acid was found in the skeletal muscle, indicating that it was in fact able to cross the intestinal wall and be transported into the muscle cells. Moreover, oral administration of 2-(carbamimidoyl-methyl-amino)ethoxyphosphonic acid allows for a more constant level in the body for about 15 hours following administration, which begins to decrease after 33 hours (Marzo A, et al. Arch. Int. Pharmacopdyn. (1971) 192, 378-392). As shown by the aforementioned experiments, since 2-(carbamimidoyl-methyl-amino)ethoxyphosphonic acid is absorbed into the cell, it can therefore act as a vehicle to move phosphate into a cell. As such, the phosphate can then be donated to high-energy molecules within the cell. The increase in intracellular, intercellular, extracellular and intratissue phosphate allows for the more rapid phosphorylation of ADP and creatine to the high energy bearing molecules to ATP and phosphocreatine as discussed above, during anaerobic conditions. Therefore, the resulting relative increase in ATP and phosphocreatine leads to longer muscular endurance as well as more forceful muscle contractions.

As discussed above, it is recognized that 2-(carbamimidoyl-methyl-amino)ethoxyphosphonic acid acts as a vehicle to transport phosphate into the cells where it can then dissociate to form the high-energy molecule ATP or to phosphorylate creatine to phosphocreatine, which can then donate the phosphate to ADP to form ATP to be used in muscular contractions. Under conditions wherein phosphate is not supplemented, it would, naturally have to be drawn from a pool of available phosphate, thereby reducing the availability of phosphate for other reactions, such as cellular signaling. Furthermore, the available phosphate existing in the somatic cells and extracellular space is already a diminutive portion of the body's totally supply of phosphate.

In one embodiment of the invention, a portion of 2-(carbamimidoyl-methyl-amino)ethoxyphosphonic acid is fine-milled. U.S. Provisional Application No. 60/776,325 entitled "Compositions and Method for Increasing Bioavailability of Compositions for Performance Improvement", which is herein fully incorporated by reference discloses a method of improving the absorption, palatability, taste, texture and bioavailability of compounds by increasing the solubility. The increased bioavailability of a compound or ingredients is achieved via a reduction in particle size using a "fine-milling" technique. Any acceptable fine-milling technique will result in the fine-milled particles having an average particle size of between about 50 nm to about 2 nm. The reduction in size of the particle increases the surface area-to-volume ratio of each particle, thus increasing the rate of dissolution, thereby improving the rate of absorption.

As used herein, the terms "fine-milled" and/or "fine-milling" refer the process of micronization. Micronization is a mechanical process which involves the application of force to a particle, thereby resulting in a reduction in the size of said particle.

As used herein, the term "particle size" refers to the diameter of the particle. The term "average particle size" means that at least 50% of the particles in a sample will have the specified particle size. Preferably, at least 80% of the particles in a given sample will have the specified particle size, and more preferably, at least 90% of the particles in a given sample will have the specified particle size Although the preceding specification describes how 2-(carbamimidoyl-methyl-amino)ethoxyphosphonic acid may be employed as an energetic molecule by way of transporting phosphate into the cell where it can act as phosphate donor to ADP and creatine, it should not be construed as the only method whereby 2-(carbamimidoyl-methyl-amino)ethoxyphosphonic acid may be employed as an energetic molecule. From consideration of the specification, those of skill in the art may determine other methods wherein 2-(carbamimidoyl-methyl-amino)ethoxyphosphonic acid may act as an energetic molecule.

What is claimed is:

1. A method of increasing intracellular phosphate, comprising the steps of:
    selecting a composition comprising creatine and fine-milled 2-(carbamimidoyl-methyl-amino)ethoxyphosphonic acid particles admixed with a comestible carrier, at least 50% of said 2-(carbamimidoyl-methyl-amino)ethoxyphosphonic acid particles having a particle size between 2-50 nm; and
    orally administering to a human an effective amount of said composition to increase intracellular concentration of phosphate.

2. The method according to claim 1, wherein said phosphate is 2,3-diphosphoglycerate.

3. The methods according to claims 1 or 2, wherein at least 80% of said fine-milled 2-(carbomimidoyl-methyl-amino)ethoxyphosphic acid particles have a particle size between 2-50 nm.

4. The methods according to claims 1 or 2, wherein at least 90% of said fine-milled 2-(carbomimidoyl-methyl-amino)ethoxyphosphic acid particles have a particle size between 2-50 nm.

5. The method according to claim 1, wherein said phosphate is increased in red blood cells.

6. The method according to claim 5, wherein said phosphate is 2,3-diphosphoglycerate.

7. The methods according to claim 6, wherein at least 80% of said fine-milled 2-(carbomimidoyl-methyl-amino)ethoxyphosphic acid particles have a particle size between 2-50 nm.

8. The methods according to claim 6, wherein at least 90% of said fine-milled 2-(carbomimidoyl-methyl-amino)ethoxyphosphic acid particles have a particle size between 2-50 nm.

9. The method according to claim 1, wherein said phosphate is increased in muscle cells.

10. The method according to claim 9, wherein said phosphate is 2,3-diphosphoglycerate.

11. The methods according to claim 10, wherein at least 80% of said fine-milled 2-(carbomimidoyl-methyl-amino)ethoxyphosphic acid particles have a particle size between 2-50 nm.

12. The methods according to claim 10, wherein at least 90% of said fine-milled 2-(carbomimidoyl-methyl-amino)ethoxyphosphic acid particles have a particle size between 2-50 nm.

* * * * *

UNITED STATES PATENT AND TRADEMARK OFFICE
CERTIFICATE OF CORRECTION

PATENT NO. : 7,368,441 B2  Page 1 of 2
APPLICATION NO. : 11/468605
DATED : May 6, 2008
INVENTOR(S) : James D. Ramsbottom et al.

It is certified that error appears in the above-identified patent and that said Letters Patent is hereby corrected as shown below:

COLUMN 1:

Line 22, "branes however," should read --branes, however--.

COLUMN 2:

Line 58, "comprises," should read --comprises--; and
Line 66, "adenosine" should be deleted.

COLUMN 3:

Lines 15-23, " 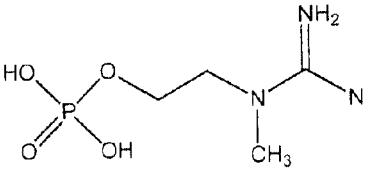 " should read

-- 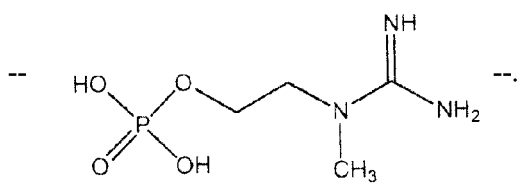 --.

COLUMN 4:

Line 46, "sparring" should read --sparing--; and
Line 58, "preformed" should read --performed--.

COLUMN 6:

Line 26, "2-(carbomimidoyl-methyl-" should read
    --2-(carbamimidoyl-methyl- --;
Line 27, "amino)ethoxyphosphic" should read --amino)ethoxyphosphonic--;
Line 30, "2-(carbomimidoyl-methyl-" should read --2-(carbamimidoyl-
    methyl- --;
Line 31, "amino)ethoxyphosphic" should read --amino)ethoxyphosphonic--;
Line 38, "2-(carbomimidoyl-methyl-amino)" should read --2-(carbamimidoyl-
    -methyl-amino)--;
Line 39, "ethoxyphosphic" should read --ethoxyphosphonic--;
Line 42, "2-(carbomimidoyl-methyl-amino)" should read --2-(carbamimidoyl-
    -methyl-amino)--;
Line 43, "ethoxyphosphic" should read --ethoxyphosphonic--;

UNITED STATES PATENT AND TRADEMARK OFFICE
CERTIFICATE OF CORRECTION

| | |
|---|---|
| PATENT NO. | : 7,368,441 B2 |
| APPLICATION NO. | : 11/468605 |
| DATED | : May 6, 2008 |
| INVENTOR(S) | : James D. Ramsbottom et al. |

It is certified that error appears in the above-identified patent and that said Letters Patent is hereby corrected as shown below:

Line 50, "2-(carbomimidoyl-methyl-amino)" should read --2-(carbamimidoyl-methyl-amino)--;
Line 51, "ethoxyphosphic" should read --ethoxyphosphonic--;
Line 54, "2-(carbomimidoyl-methyl-amino)" should read --2-(carbamimidoyl-methyl-amino)--; and
Line 55, "ethoxyphosphic" should read --ethoxyphosphonic--.

Signed and Sealed this

Sixteenth Day of September, 2008

JON W. DUDAS
*Director of the United States Patent and Trademark Office*